US009888863B2

(12) United States Patent
Biancolillo et al.

(10) Patent No.: US 9,888,863 B2
(45) Date of Patent: *Feb. 13, 2018

(54) METHOD AND DEVICE FOR MEASURING ELECTRICAL IMPEDANCE OF BIOLOGIC TISSUES

(75) Inventors: Pasquale Biancolillo, Pedara (IT); Stefano Rossi, Siena (IT); Giuseppe Bruno, Paterno' (IT); Angelo Recchia, Fasano (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 1402 days.

This patent is subject to a terminal disclaimer.

(21) Appl. No.: 13/534,778

(22) Filed: Jun. 27, 2012

(65) Prior Publication Data

US 2013/0006136 A1 Jan. 3, 2013

(30) Foreign Application Priority Data

Jun. 28, 2011 (IT) ................. MI2011A1177

(51) Int. Cl.
 *A61B 5/05* (2006.01)
 *A61B 5/053* (2006.01)
 (Continued)

(52) U.S. Cl.
 CPC ......... *A61B 5/0535* (2013.01); *G01N 27/028* (2013.01); *A61B 5/6804* (2013.01)

(58) Field of Classification Search
 CPC ...................................................... A61B 5/00
 (Continued)

(56) References Cited

U.S. PATENT DOCUMENTS

| 4,909,261 A | 3/1990 | Rothenberg |
| 5,179,946 A * | 1/1993 | Weiss ............ A61N 1/3962 |
| | | 600/547 |

(Continued)

FOREIGN PATENT DOCUMENTS

| IT | VA20100078 | 8/2011 |
| IT | VA20100017 | 4/2012 |
| JP | 57191567 | 11/1982 |

OTHER PUBLICATIONS

Gonzalez-Landaeta et al., Heart Rate Detection From Plantar Bioimpedance Measurements, Mar. 2008, pp. 1163-1167.

(Continued)

*Primary Examiner* — Rene Towa
*Assistant Examiner* — May Abouelela
(74) *Attorney, Agent, or Firm* — Slater Matsil, LLP

(57) ABSTRACT

A device for measuring an electrical impedance of biologic tissue may include electrodes configured to contact the biologic tissue and generate a differential voltage thereon. The device may include a first circuit coupled to the electrodes and configured to force an oscillating input signal therethrough, and a differential amplitude modulation (AM) demodulator coupled to the plurality of electrodes. The differential AM demodulator may be configured to demodulate the differential voltage, and generate a base-band signal representative of the demodulated differential voltage. The device may further include an output circuit downstream from the differential AM demodulator and may be configured to generate an output signal representative of the electrical impedance as a function of the base-band signal.

17 Claims, 12 Drawing Sheets

(51) Int. Cl.
*G01N 27/02* (2006.01)
*A61B 5/00* (2006.01)

(58) Field of Classification Search
USPC .......................................................... 600/547
See application file for complete search history.

(56) References Cited

U.S. PATENT DOCUMENTS

| | | | | |
|---|---|---|---|---|
| 5,503,157 | A * | 4/1996 | Sramek | A61B 5/0535 600/506 |
| 6,076,015 | A * | 6/2000 | Hartley | A61N 1/36521 600/547 |
| 6,377,845 | B1 * | 4/2002 | Kinast | A61B 5/0535 600/547 |
| 6,961,614 | B2 * | 11/2005 | Kaye | A61B 5/0538 600/547 |
| 8,594,779 | B2 * | 11/2013 | Denison | A61B 5/0478 600/544 |
| 8,706,208 | B2 * | 4/2014 | Chiao | 600/350 |
| 2002/0161310 | A1 * | 10/2002 | Daum | A61N 1/36521 600/547 |
| 2004/0082946 | A1 * | 4/2004 | Malis | A61B 18/1206 606/34 |
| 2006/0041280 | A1 * | 2/2006 | Stahmann | A61B 5/053 607/17 |
| 2008/0221477 | A1 * | 9/2008 | Olson | A61B 5/053 600/547 |
| 2008/0234599 | A1 * | 9/2008 | Chiao | A61B 5/0031 600/547 |
| 2008/0275361 | A1 * | 11/2008 | Loriga | A61B 5/0535 600/547 |
| 2009/0024044 | A1 * | 1/2009 | Virtanen | A61B 5/0205 600/509 |
| 2009/0177110 | A1 * | 7/2009 | Lyden | A61B 5/029 600/547 |
| 2009/0234262 | A1 | 9/2009 | Reid, Jr. et al. | |
| 2010/0198101 | A1 * | 8/2010 | Song | A61B 5/0536 600/547 |
| 2011/0046505 | A1 * | 2/2011 | Cornish | A61B 5/053 600/547 |
| 2011/0054343 | A1 * | 3/2011 | Chetham | A61B 5/053 600/547 |
| 2011/0074442 | A1 * | 3/2011 | Min | A61B 5/053 324/647 |
| 2011/0208028 | A1 | 8/2011 | Rossi | |
| 2011/0208083 | A1 * | 8/2011 | Gutfinger | A61B 5/04011 600/547 |
| 2011/0245712 | A1 * | 10/2011 | Patterson | A61B 5/0535 600/547 |
| 2013/0102920 | A1 * | 4/2013 | Fan | A61B 5/053 600/547 |

OTHER PUBLICATIONS

Kim, Detection of Physiological Events by Impedance, Yonsei Medical Journal, vol. 30, No. 1, Jan. 27, 1989, pp. 1-11.

* cited by examiner

METHOD AND DEVICE FOR MEASURING ELECTRICAL IMPEDANCE OF BIOLOGIC TISSUES

FIELD OF THE INVENTION

This invention relates to measurement instruments, and more particularly, to a method and relative device for sensing modulus and phase or a real part and an imaginary part of the electrical impedance of biologic tissues.

BACKGROUND OF THE INVENTION

Measurements of electrical impedance of the human body (bioimpedance) have been studied, in bioengineering, since 1960s. These measurements include forcing an alternating current (AC) through the body (usually at a frequency higher than 10 kHz to reduce interference with the electrical activity of nervous and muscular tissues), and sensing the voltage drop between two points.

Water and body fluids (blood, intra and extra cellular fluid, for example) provide the conductive medium. Several measures and studies have been conducted by applying this technique in different parts or regions of the body and using different frequencies to target different biological information (See for example, Deok-Won Kim, *Detection of physiological events by impedance*, Yonsei Medical Journal, 30(1), 1989). In numerous applications only the absolute value of the bioimpedance is to be determined because it is easier to calculate and provides much information. In other applications, both modulus and phase of the complex bioimpedance are measured.

It may be a relatively difficult to determine precise and reliable mathematical models of bioimpedance, particularly in the thoracic region. The main factors influencing electrical impedance in the chest are: the blood present in the heart and in the aorta; and the pleural fluids and the pulmonary circulation. Heart pumping, causing a varying spatial distribution of blood in the heart-aorta region, and respiration cause non-negligible variations of thoracic bioimpedance (i.e. the impedance of biologic tissues). From these variations it may even be possible to determine heart rate, breath rate, and evaluate cardiac output (volume of blood pumped by the heart for unity of time).

The measurements may be carried out using two or four electrodes, as schematically shown in FIG. 1. When using two electrodes, the measured impedance is the sum of the bioimpedance Zbody and of the contact impedance Ze at the electrodes. Generally, the impedance Ze disturbs the measurement of the impedance Zbody. Using a more refined four electrode setup, it may be possible to measure the impedance Zbody as a ratio between the measured voltage drop and the current forced through the body tissues with increased precision, because the measurement is no longer affected by the contact impedance Ze.

There is an increasing interest about methods of carrying out these measurements, because it is generally a non-invasive technique and may be correlated to a vast range of physiological parameters. Thus it may be seen as having a strong potential in many medical fields. Furthermore, simplicity of measurements, integratability, reduced size, and low cost of the equipment, may make the technique of measuring thoracic bioimpedance particularly suitable to be implemented in wearable or implantable health monitoring systems.

Generally, the voltage $V_Z(t)$ sensed on the electrodes is an AC signal that is modulated by the bioimpedance $Z(t)$;

$$V_Z(t)=Z(t)I_0 \sin(\omega t)$$

With an AM demodulator it may be possible to obtain a base-band signal representing the modulus $|Z(t)|$ of the impedance. The phase of $Z(t)$ may be evaluated, for example, by measuring the delay between the input current and output voltage or with a phase and quadrature demodulation.

A block diagram of a typical circuit for measuring the impedance of a biologic tissue is illustrated in FIG. 2. An AC voltage generated by an oscillator is used to control a voltage-to-current converter that delivers a current Iz that is injected through the biologic tissue using two or four electrodes. The voltage on the biologic tissue is sensed, amplified, and AM demodulated for obtaining a base-band signal. The DC component Z0 and the AC component deltaZ of the obtained base-band signal are extracted using a low-pass filter LPF and a high-pass filter HPF and converted into digital form by an analog-to-digital converter ADC. This type of system is characterized by the presence of an instrumentation amplifier (INA) upstream the AM demodulator.

A drawback of such a signal processing path is the fact that the INA operates on the modulated input signal. For this reason, the known architecture of FIG. 2 requires either an INA of sufficiently large bandwidth and thus having a large current consumption, or the use of a relatively low frequency of the current that is injected in the body tissues for carrying out the measurement. This is a limitation, because INAs, especially low power consumption and low cost devices, usually have a relatively narrow bandwidth.

U.S. patent application publication No. 2009/234,262 discloses a device for measuring the impedance of a biologic tissue having a differential amplifier connected to the electrodes and an AM demodulator of the differentially amplified signal. This prior device has the same drawbacks of the prior device of FIG. 2.

Another known measurement system is depicted in FIG. 3, as disclosed in Rafael González-Landaeta, Oscar Casas, and Ramon Pallás-Areny, Heart rate detection from plantar bioimpedance measurements, IEEE Transactions on Biomedical Engineering, 55(3):1163-1167, 2008. AM demodulation is performed upstream the INA to increase the CMRR. The circuitry is fully differential and a differential stage with coupled amplifiers is used as first stage of the voltage drop on the electrodes. A high pass filter HPF and amplifier stage is used for extracting the AC components of the signal, deltaZ, that in many applications (for example thoracic bioimpedance measurement), including important physiological information.

By resuming, in the cited prior devices, there is an input amplification stage for amplifying (and, eventually, filtering) the signals collected on the electrodes and, downstream, a demodulation circuit for extracting the base-band components thereof.

U.S. Pat. No. 4,909,261 discloses a device for measuring impedances of biologic tissues that has two pairs of electrodes coupled through transformers to a circuit. The circuit applies a same AC voltage to the electrodes. The device also includes as many differential AM demodulators, each coupled to a respective pair of electrodes through a respective transformer. A circuit combines the AC and DC components of the two AM demodulated signals for measuring the impedance of the biologic tissue.

Each AM signal to be differentially demodulated is collected on the same pair of electrodes used to force current throughout a respective portion of the biologic tissue. Therefore, this prior device combines two demodulated AM signals not pertaining to the same portion of biologic tissue. Moreover, the presence of transformers may not make it suited for wearable applications.

A device that does not require any differential amplifier of the sensed voltage on the electrodes is disclosed in prior Italian patent application No. VA2010A000017, the applicant of which is the same as the present applicant. The device includes two single-ended AM demodulators respectively of the voltages towards ground of two electrodes, a differential amplifier of the base-band demodulated single-ended voltages, and a filter for extracting the DC and the AC components of the differential base-band voltage. An output circuit is adapted to generate an output signal representative of the impedance corresponding to the DC component of the base-band voltage.

SUMMARY OF THE INVENTION

Studies carried out by the applicant have led to the recognition that it is possible to realize a device implementing a related method of measuring electrical impedance of biologic tissues, particularly adapted for wearable applications. The device embeds at least a differential amplitude modulation (AM) demodulator of the voltage present on the electrodes. The differential AM demodulator generates a base-band signal, that eventually may be amplified with a low cost amplifier, from which an output circuit may generate output signals of the device representing the impedance of the biologic tissue between the electrodes.

According to an embodiment adapted to estimate the real part and the imaginary part of bioimpedances, the device includes a second differential AM demodulator, one demodulating the differential voltage on the electrodes with a carrier in phase with the current injected throughout the biologic tissue by the electrodes. The device also includes the other AM demodulator demodulating the same differential voltage with a second carrier in quadrature in respect to the first carrier. Preferably, the first and second carriers are square-wave oscillating signals, and the output circuit of the device generates signals representative of the real part and of the imaginary part of the impedance in the complex domain by processing the signals generated by the two AM demodulators according to two parametric polynomial functions.

According to a particular embodiment of the method of measuring impedance of biologic tissues, the parameters of the two parametric polynomial functions are adjusted using values stored in a look-up table using as entry value either:
  the phase difference between the voltage on the electrodes and the current forced throughout the biologic tissue, or
  the ratio between the demodulated signals generated by the two differential AM demodulators.

DETAILED DESCRIPTION OF THE PREFERRED EMBODIMENTS

Figure 3:
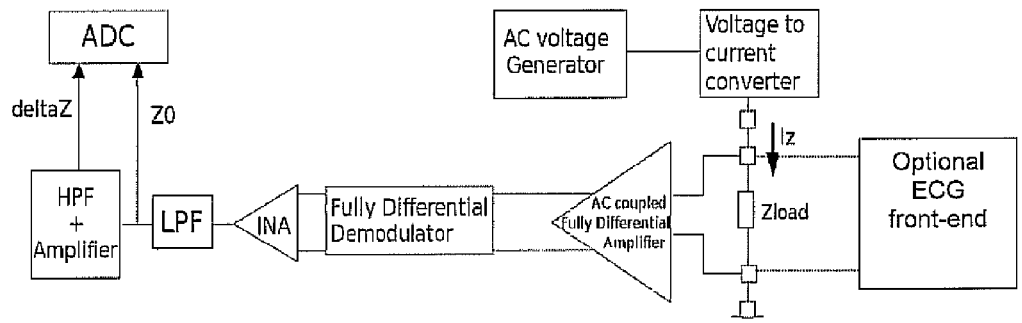
FIG. 3 is a schematic diagram of an architecture disclosed in Rafael González-Landaeta, Oscar Cases, and Ramon Pallás-Areny, *Heart rate detection from plantar bioimpedance measurements*, IEEE Transactions on Biomedical Engineering, 55(3):1163-1167, 2008 for measuring impedance of biologic tissues in accordance with the prior art.
Figure 4:
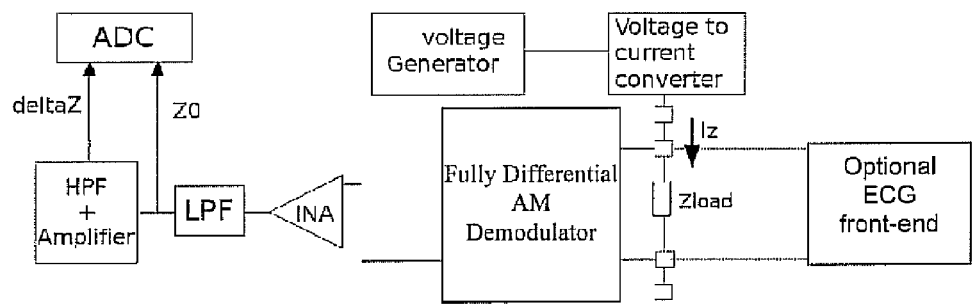
FIG. 4 is a schematic diagram of a device for measuring impedance of biologic tissues having a differential AM demodulator directly connected to the electrodes in accordance with the present invention.

An embodiment of a device for measuring the impedance of biologic tissues is illustrated in FIG. 4. The circuit blocks in common with the prior devices of FIGS. 2 and 3 are identified by the same labels.

The applicant found that it is not necessary to amplify the voltage on the electrodes that inject a current throughout a biologic tissue, and thus, that it is possible to connect directly the AM differential demodulator directly to the electrodes as shown in FIG. 4. The demodulated base-band signal is, in most practical cases, adapted to be amplified and processed for generating signals representing with a sufficient accuracy the modulus and the phase of the impedance in the complex domain. The so AM demodulated base-band differential signal may be supplied in input to an INA, that generates an amplified replica thereof.

Figure 1:
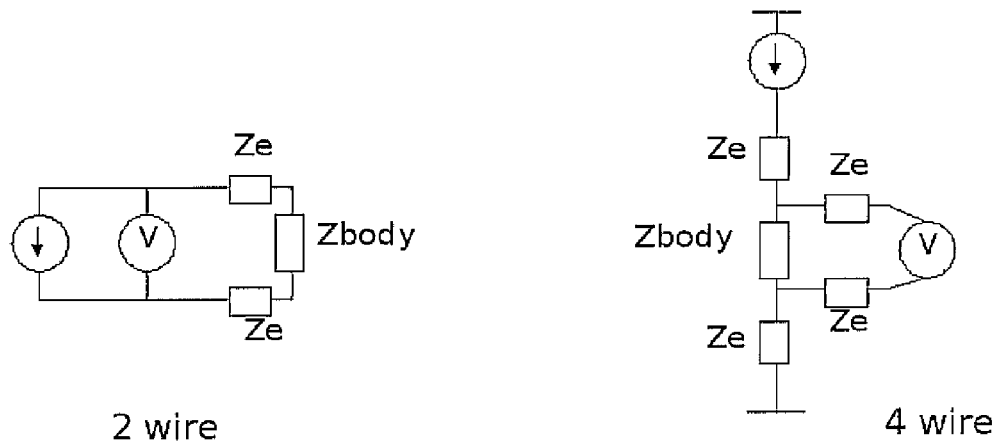
FIG. 1 illustrates two architectures for measuring the impedance of a biologic tissue in accordance with the prior art.
Figure 2:
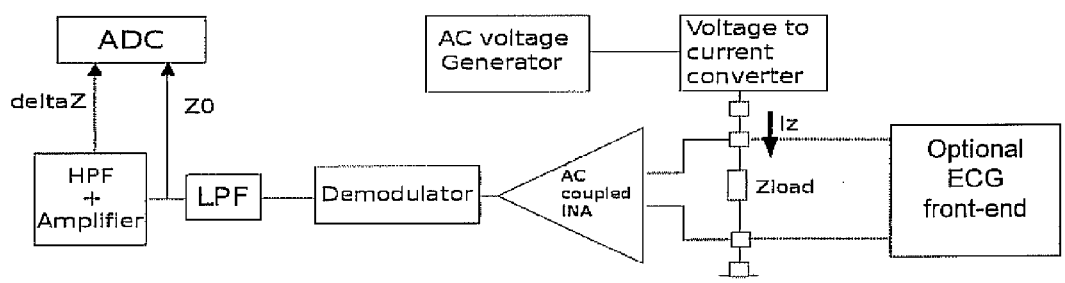
FIG. 2 is a schematic diagram of an architecture for measuring the impedance of a biologic tissue in accordance with the prior art.

Differently from the known device of FIG. 2, the INA amplifies always a base-band signal, thus it has a large gain and a relatively good CMRR in the base-band range of frequencies. Therefore it is possible to use a low cost and low power consumption INA.

According to an embodiment, the voltage generator VOLTAGE GENERATOR generates a sinusoidal voltage, to force a sinusoidal current throughout the electrodes. According to a more preferred embodiment, throughout the electrodes, a square-wave current is forced and the AM demodulated base-band signal is obtained by demodulation using a square-wave demodulating carrier. Therefore, in this particular case the block VOLTAGE GENERATOR generates a square-wave voltage that is converted into a square-wave current injected throughout the biologic tissue. In this embodiment the realization of the differential AM demodulator is simplified and the resulting AM demodulated base-band signal may be processed, as will be shown hereinafter, to generate signals that represent accurate estimations of the modulus and the phase (or of the real part and of the imaginary part) of the impedance.

Figure 5:
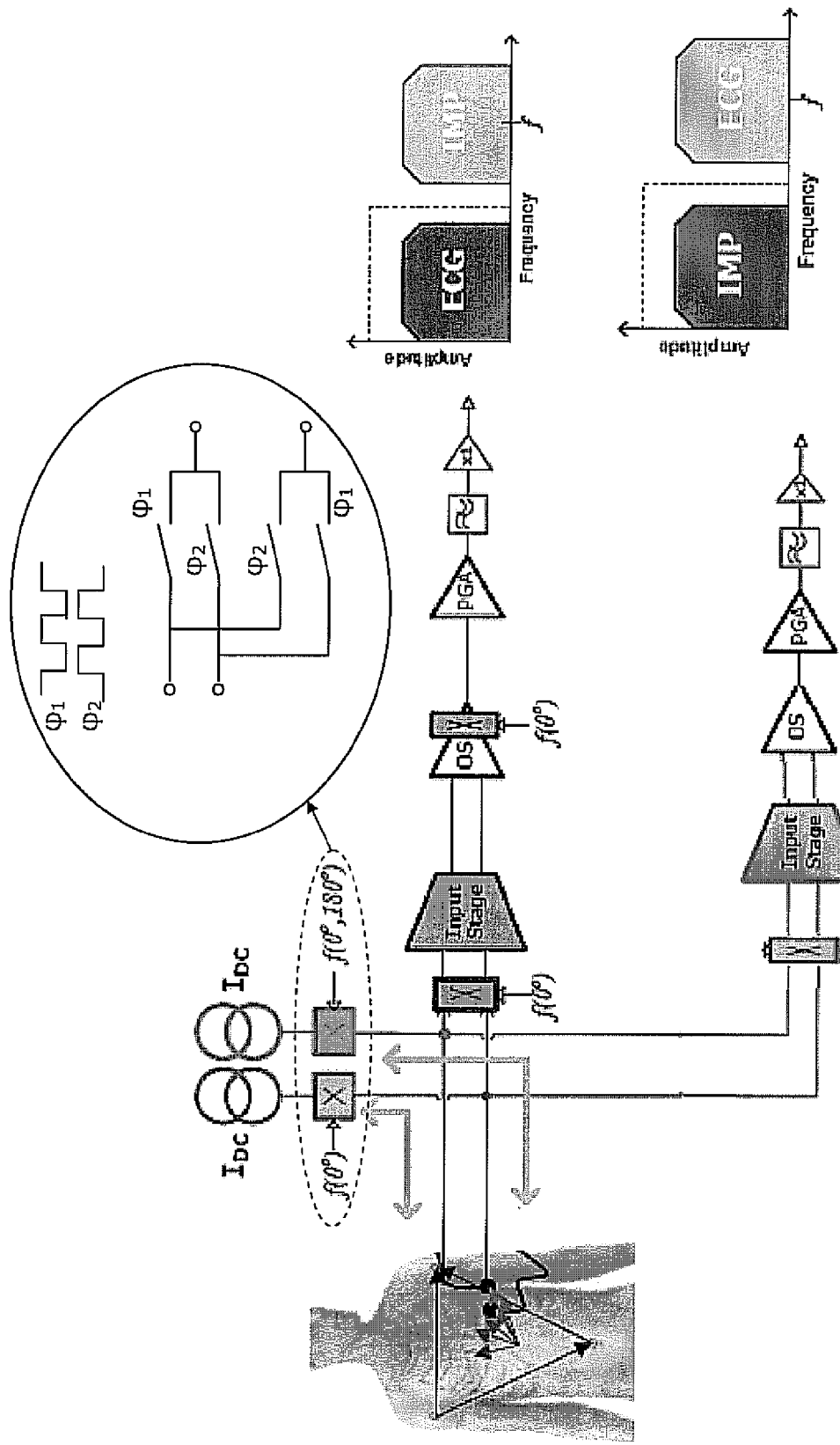
FIG. 5 is a device generating an electrocardiogram (ECG), having a channel for sensing the impedance of biologic tissues using a square-wave AM demodulating carrier in accordance with the present invention.

In a four electrode configuration, as the architecture shown in FIG. 4, it is optionally possible to connect an ECG front-end to measure also the electrocardiogram of a patient. An architecture of a device for measuring the impedance of biologic tissues and for generating an ECG of a patient is illustrated in FIG. 5. The blocks X include two pairs of switches controlled in phase opposition by the control phases $\phi_1$ and $\phi_2$, as shown in FIG. 5. The function of each block is resumed in the following table:

| | |
|---|---|
| INPUT STAGE | Instrumentation Amplifier stage |
| OS | Output stage with chopping spike filter |
| PGA | Programmable Gain Amplifier |
| ≈ | Analog Filter |
| x1 | Voltage buffer |
| X | Chopper switches |

The frequency spectra on the right side of FIG. 5 highlights that the output of the channel at the top of the figure is the sum of a base-band signal representing the ECG of the patient and of a modulated signal at the switching frequency f of the square-waves $\phi_1$ and $\phi_2$, that represent the impedance of the biologic tissue between the electrodes. The channel at the bottom of the figure outputs the sum of a base-band signal representing the impedance of the biologic tissue between the electrodes and of a modulated signal at the switching frequency f of the square-waves $\phi_1$ and $\phi_2$, that represent the ECG of the patient. Low-pass filters (not shown in the figure) extract the base-band signals representing the ECG and the impedance from the output signals of the two channels.

Injecting a square-wave current throughout the biologic tissue greatly simplifies the architecture of the differential AM demodulator and also of the AM modulator. Moreover, using a differential AM demodulator immediately downstream from the electrodes without interposing any signal processing stage between the demodulator and the electrodes, allows the use of an amplification stage INPUT STAGE with a reduced bandwidth, because it has to amplify a base-band signal.

Figure 6:
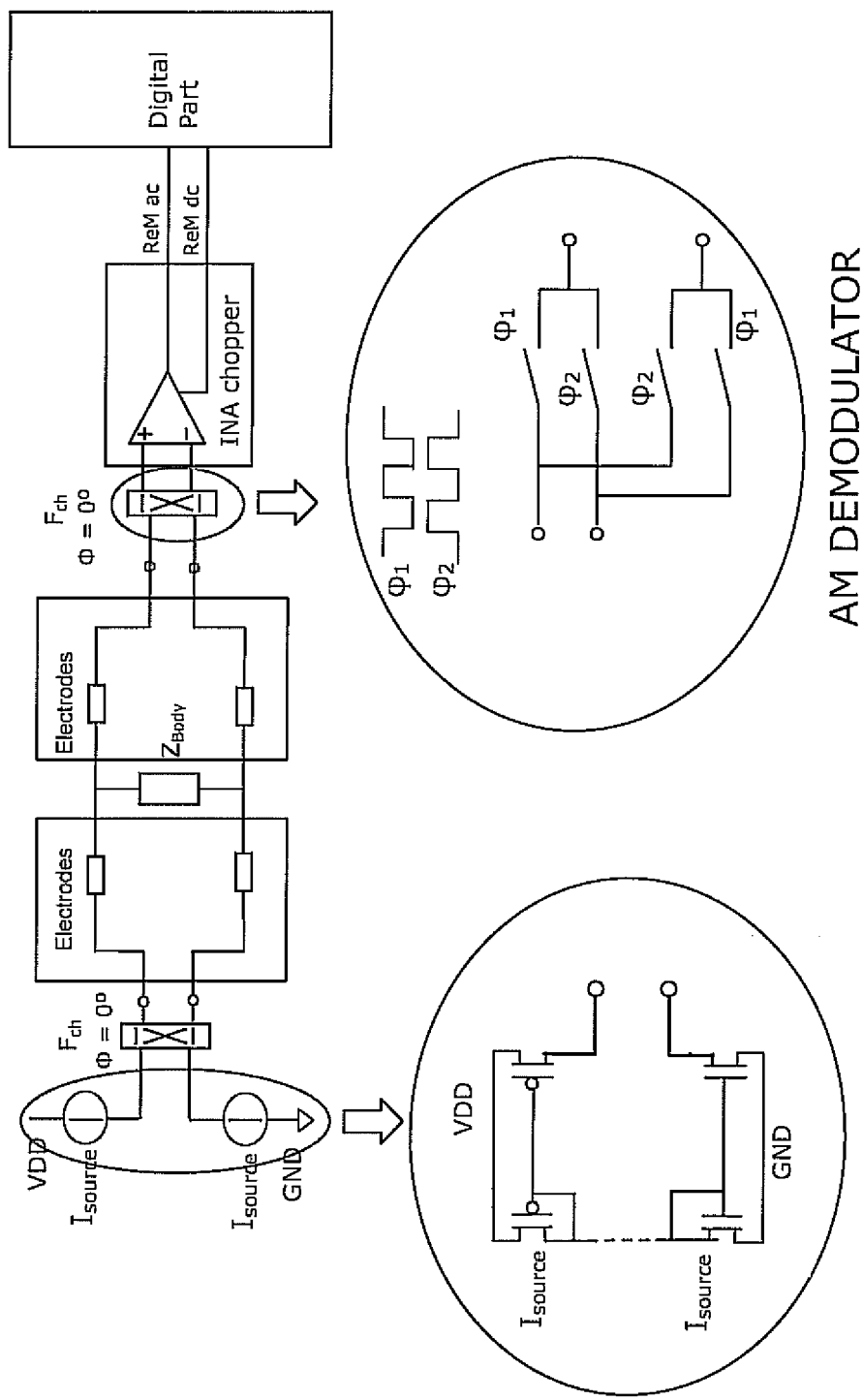
FIG. 6 is a more detailed schematic diagram of another architecture of the device that uses a square-wave AM demodulating carrier for sensing the AC and the DC components of the real part of the impedance in the complex domain in accordance with the present invention.

A more detailed representation of an architecture of a device for measuring electrical impedance of biologic tissues is illustrated in FIG. 6. Given that the current injected throughout the biologic tissue is a square-wave, the AM demodulator immediately downstream the electrodes may be easily realized with two pairs of switches controlled in phase opposition by the control phases $\phi_1$ and $\phi_2$. In the embodiment of FIG. 6, the amplifier INA generates signals that represent the AC (ReM AC) and the DC (ReM DC) components of the real part ReM of the impedance in the complex domain. A digital circuit DIGITAL PART processes the signals ReM AC and ReM DC and generates signals representing the modulus and the phase of the impedance of the biologic tissue under test.

In some applications, the parameter of interest is the modulus of the bioimpedance, that may be roughly approximated with the real part of the impedance in the complex domain, that is greater than the imaginary part. According to a more accurate method of estimating the modulus of the bioimpedance, the demodulating carrier is resynchronized with the sensed voltage on the electrodes using the technique disclosed in Italian patent application No. VA2010A000078 in the name of the applicant of the present application. Both the above mentioned methods may be relatively easily implemented with the devices disclosed herein.

Figure 7:
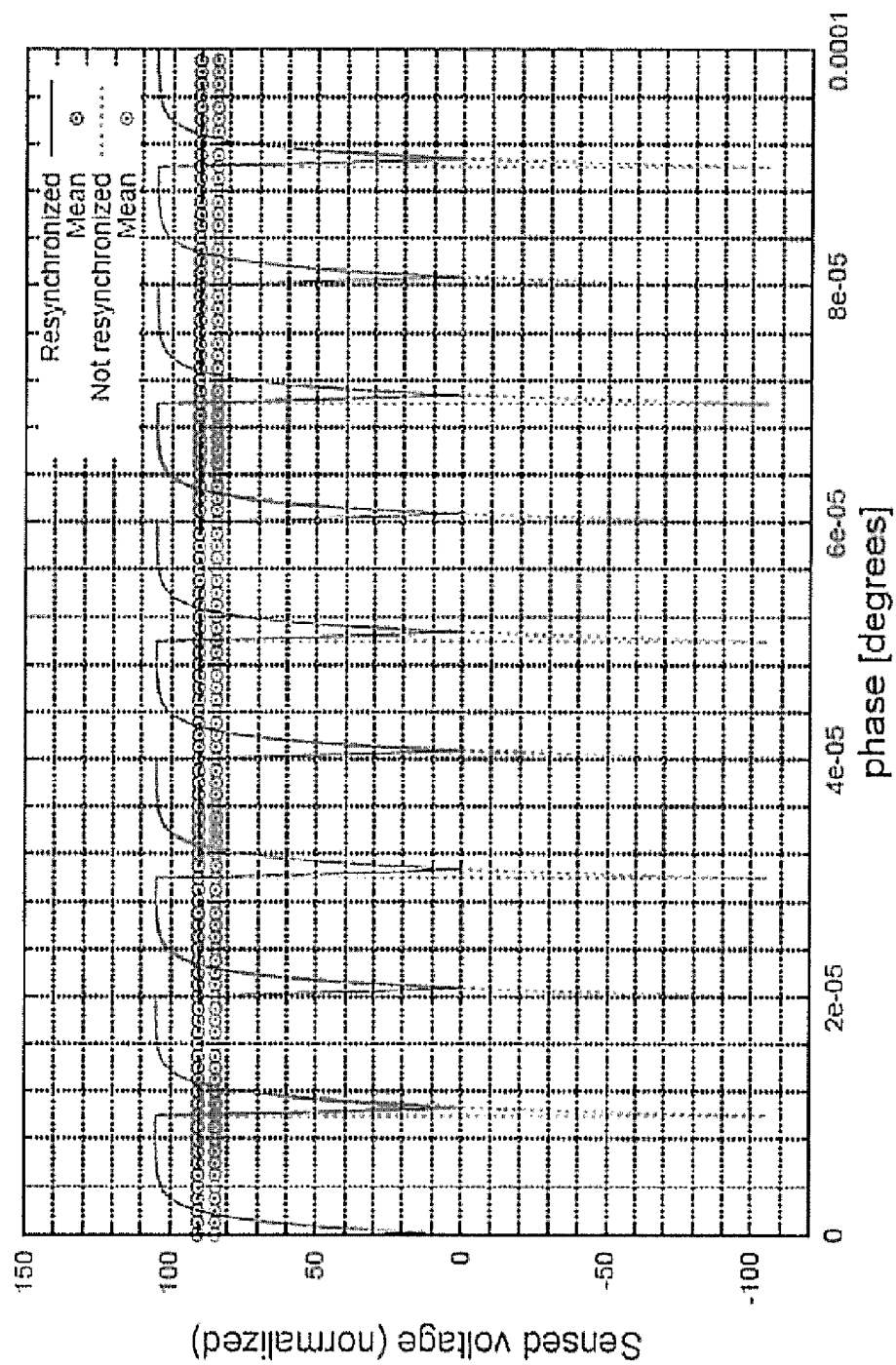
FIG. 7 is a graph of the voltage on the electrodes vs. the phase of the impedance in the complex domain when a resynchronization technique is implemented and when it is not implemented.
Figure 8:
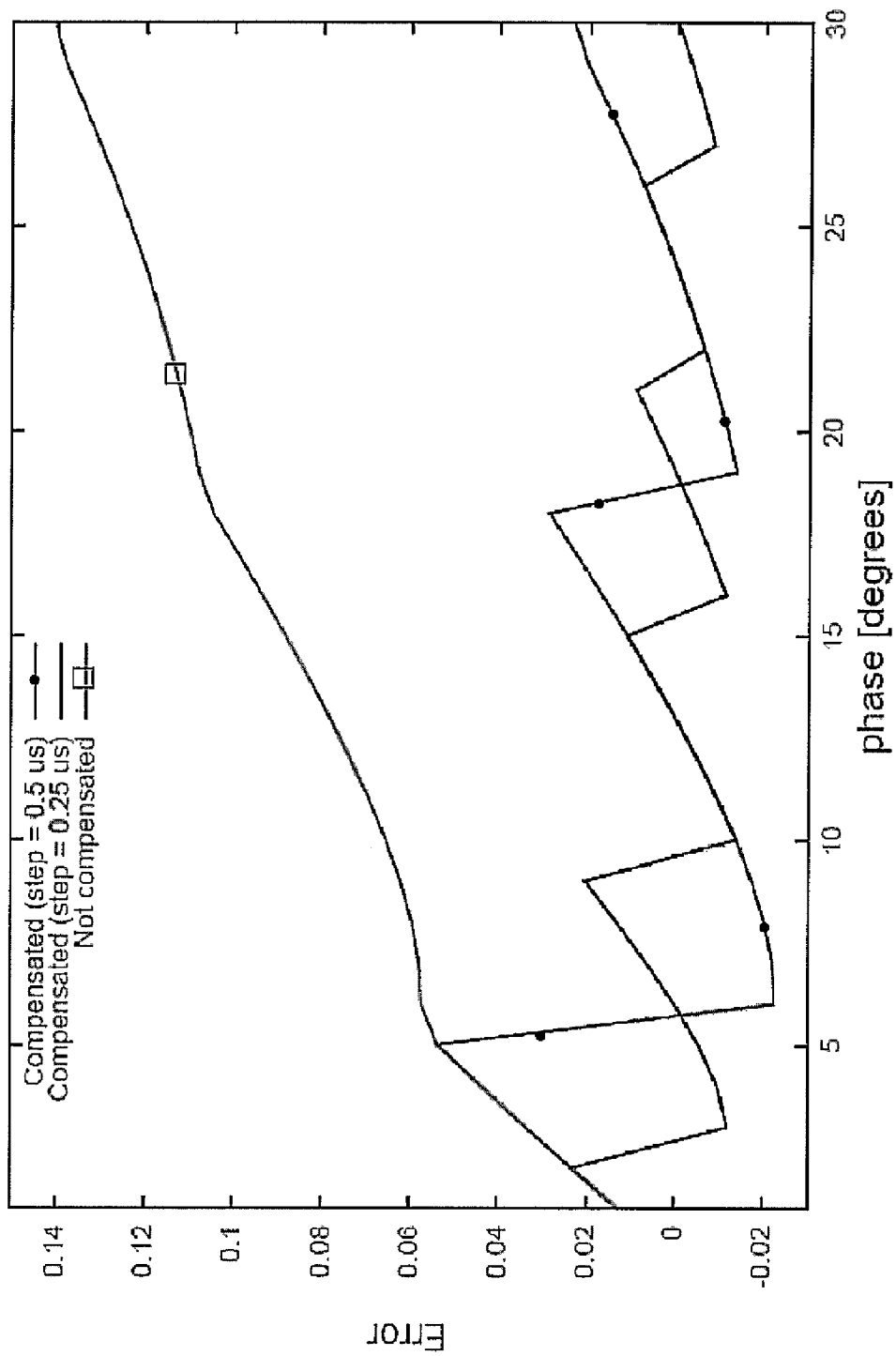
FIG. 8 is a graph of a test case of the error in estimating the modulus of the impedance vs. the phase thereof with and without using a compensation technique.
Figure 10:
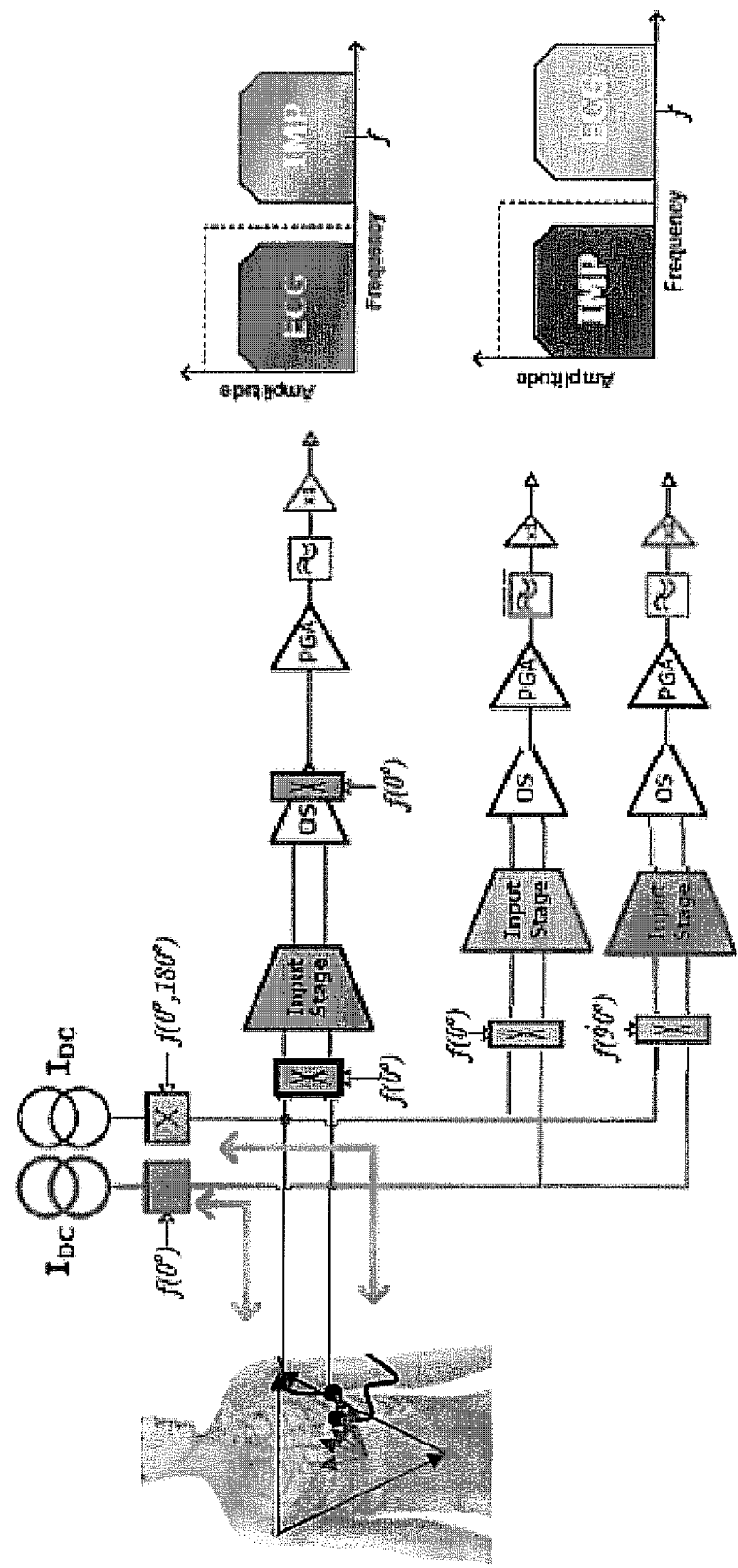
FIG. 10 is a schematic diagram of an embodiment of a device for measuring impedance of biologic tissues having two differential AM demodulators directly connected to the electrodes in accordance with the present invention.

In particular, the method disclosed in the Italian patent application No. VA2010A000078 may be implemented in the device of FIG. 10, even if this prior method has been disclosed only for AC currents injected throughout the tissue, and allows accurate estimation of the modulus of the bioimpedance. For illustrative purposes, the graph of FIG. 7 compares, obtained in a test case, the voltages sensed on the electrodes and the mean values thereof (that estimate the modulus of the bioimpedance) when a square-wave current is injected in a biologic tissue with and without applying the resynchronization technique disclosed in the cited prior Italian patent application, assuming that the correct value of the modulus of the bioimpedance is 100. It is evident that the resynchronization technique relevantly improves the accuracy of the estimations given by the mean values of the sensed voltages. The graph in FIG. 8 illustrates the corresponding percentage error vs. the phase of the bioimpedance without implementing the cited prior resynchronization technique and implementing it with different resynchronization steps.

Figure 9:
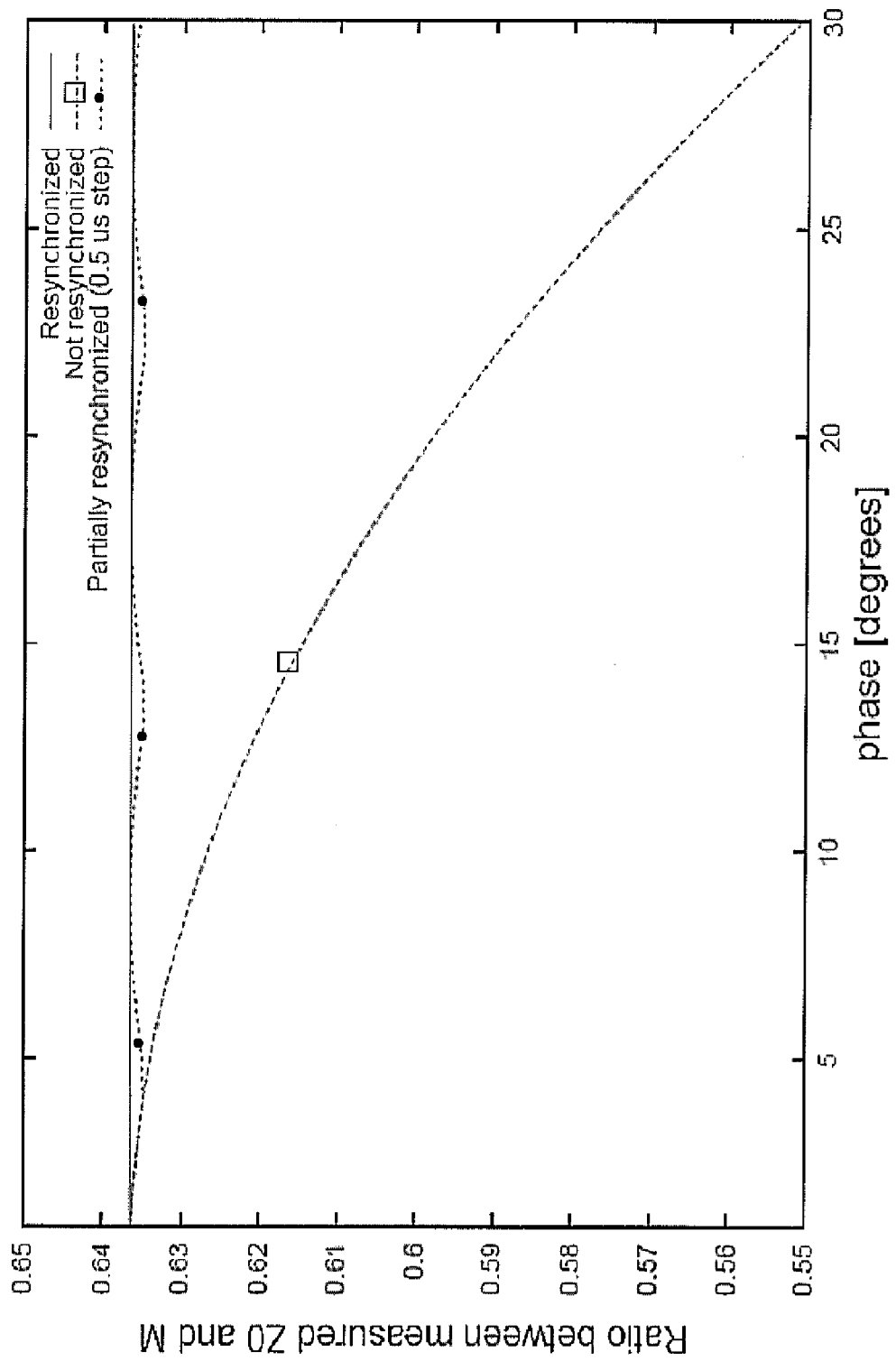
FIG. 9 is a graph of the ratio between an impedance modulus Z0 estimated by injecting a sinusoidal current with the electrodes and by using a demodulating square-wave and the effective modulus M of the impedance of a biologic tissue for various phase angles of the impedance in the complex domain, with and without applying a resynchronization technique.

It is also possible to estimate the impedance of biologic tissues by forcing an AC sinusoidal current therethrough, and by demodulating the voltage on the electrodes with a square-wave carrier. In this case, only the main harmonic of the square-wave demodulating carrier contributes in generating the base-band AM demodulated signal. For this reason, the graph of the ratio between the amplitude Z0 of the base-band signal and the modulus M of the bioimpedance is as shown in FIG. 9, as a function of the phase difference between the voltage on the electrodes and the square-wave demodulating carrier.

Therefore, the modulus M of the bioimpedance may be obtained by multiplying the amplitude Z0 of the base-band signal by a correction factor k:

$$M = k * Z0.$$

The values of the correction factor k for various phase angles may be heuristically estimated with tests and stored in a look-up table. With this technique, when the phase angle of the bioimpedance is known, for example, by using a resynchronization technique as disclosed in Italian patent application No. VA2010A000078, it may be possible to determine the value of the correction factor k, and thus obtain the modulus of the bioimpedance.

Another architecture of the device with two demodulation channels for determining in-phase and quadrature components of the bioimpedance in the complex domain is shown in FIG. 10. The blocks with the same name of those of FIG. 5 have the same function. Taking into consideration what has been stated for the architecture of FIG. 5, the functioning of the architecture of FIG. 10 will be immediately evident and for this reason this last architecture will not be further described.

Figure 11:
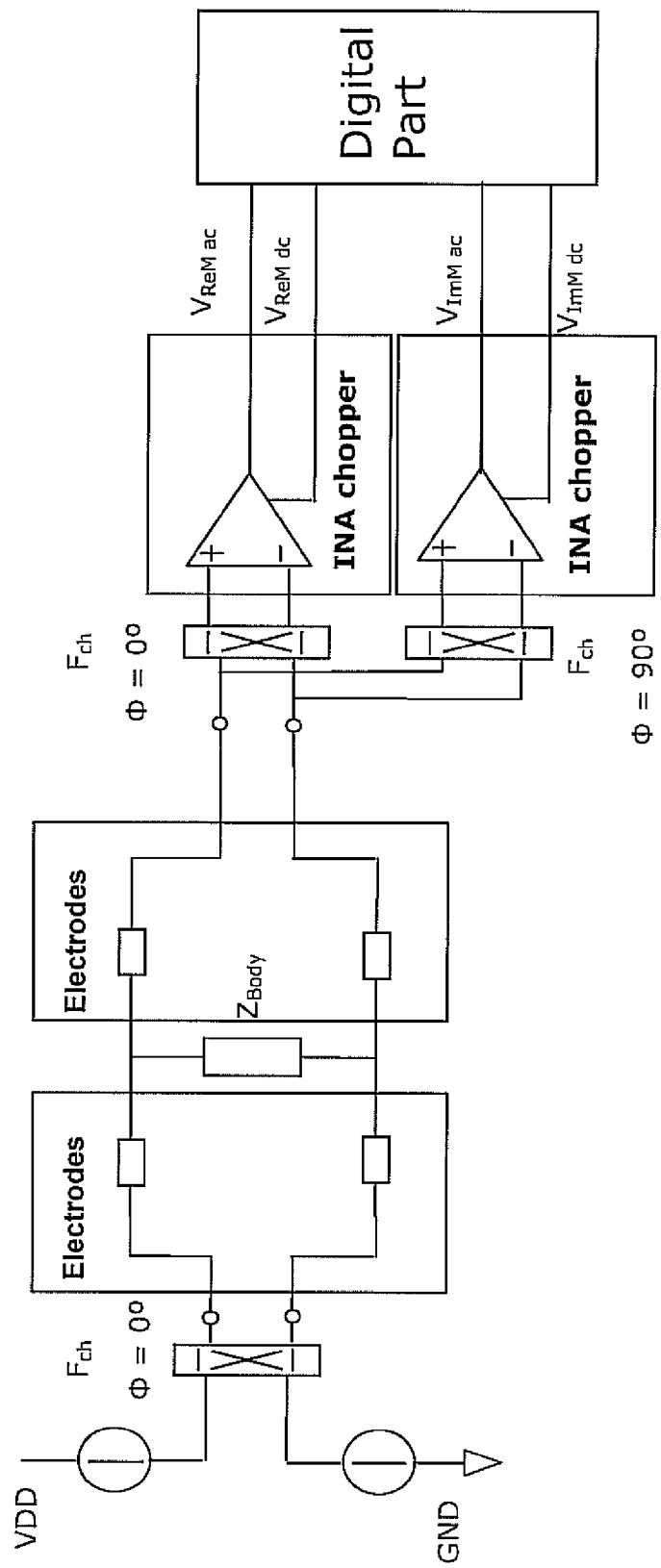
FIG. 11 is a schematic diagram of a two-channel architecture of a device that uses square-wave AM demodulating carriers in quadrature for generating signals representing the real part and the imaginary part of the impedance in the complex domain in accordance with the present invention.

An architecture similar to that of FIG. 6 for the device of FIG. 10 is illustrated in FIG. 11. Differently from the embodiment depicted in FIG. 6, the voltage on the electrodes is AM demodulated with a square-wave carrier in phase ($\phi=0°$) and in quadrature ($\phi=90°$) to generate signals that represent the AC and DC components of the real part $V_{ReM}$ and of the imaginary part $V_{ImM}$ of the bioimpedance in the complex domain.

Figure 12B:
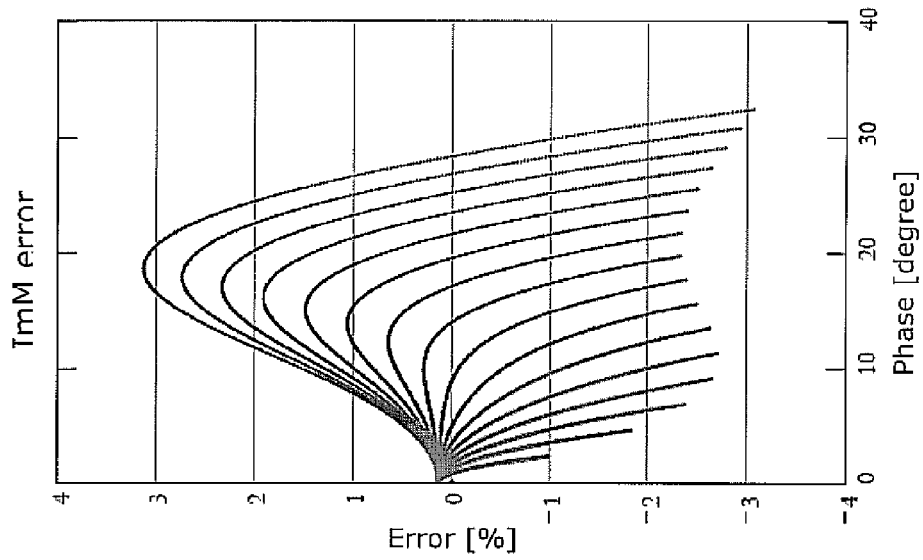
FIGS. 12*a* and 12*b* are graphs of percentage error on the estimation of the real part and of the imaginary part vs. the phase of the impedance in the complex domain.
Figure 12A:
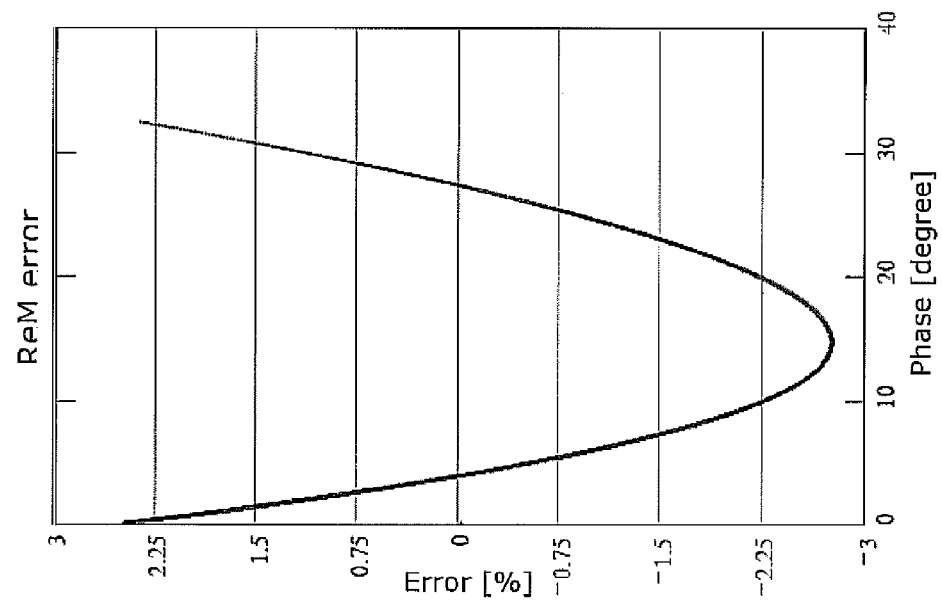

Exemplary graphs of percentage error vs. the phase of the bioimpedance in the complex domain for the real part ReM and for the Imaginary part ImM thereof are illustrated in FIGS. 12a and 12b.

According to an innovative aspect, the signals $V_{ReM}$ and $V_{ImM}$ are processed by the block DIGITAL PART for generating signals representing in a very accurate fashion the effective modulus and phase of the bioimpedance. This is done substantially by calculating the effective real ReC and imaginary ImC parts of the bioimpedance using the following parametric equations:

$$ReC = b_R * V_{ReM} + c_R * V_{ImM}$$

$$IMC = b_I * V_{ImM} + c_I * V_{ImM}^2$$

wherein $b_R$, $c_R$, $b_I$ and $c_I$ are fixed parameters.

According to an embodiment, the impedance is assumed capacitive-resistive, and the parameters $b_R$, $c_R$, $b_I$ and $c_I$ are about equal to 0.0606, −0.02, 0.093 and 0.0000056, respectively. As a general rule, the values of the parameters $b_R$, $c_R$, $b_I$ and $c_I$ depend on the working frequency and may be heuristically determined with tests depending on the application and stored in a look-up table in function of the values of the signals $V_{ReM}$ and $V_{ImM}$.

According to another embodiment, the parameters $c_R$ and $c_I$ are null, and the values of the parameters $b_R$ and $b_I$ are adjusted according to the following procedure:

preliminarily filling-in a look-up table of heuristically determined values of the parameters $b_R$ and $b_I$ as a function of phase differences between the square wave input current and the corresponding differential voltage; sensing the phase difference between the square wave input current and the corresponding differential voltage; and updating the values of the parameters $b_R$ and $b_I$ with the values stored in the look-up table corresponding to the sensed phase difference.

Figure 14:
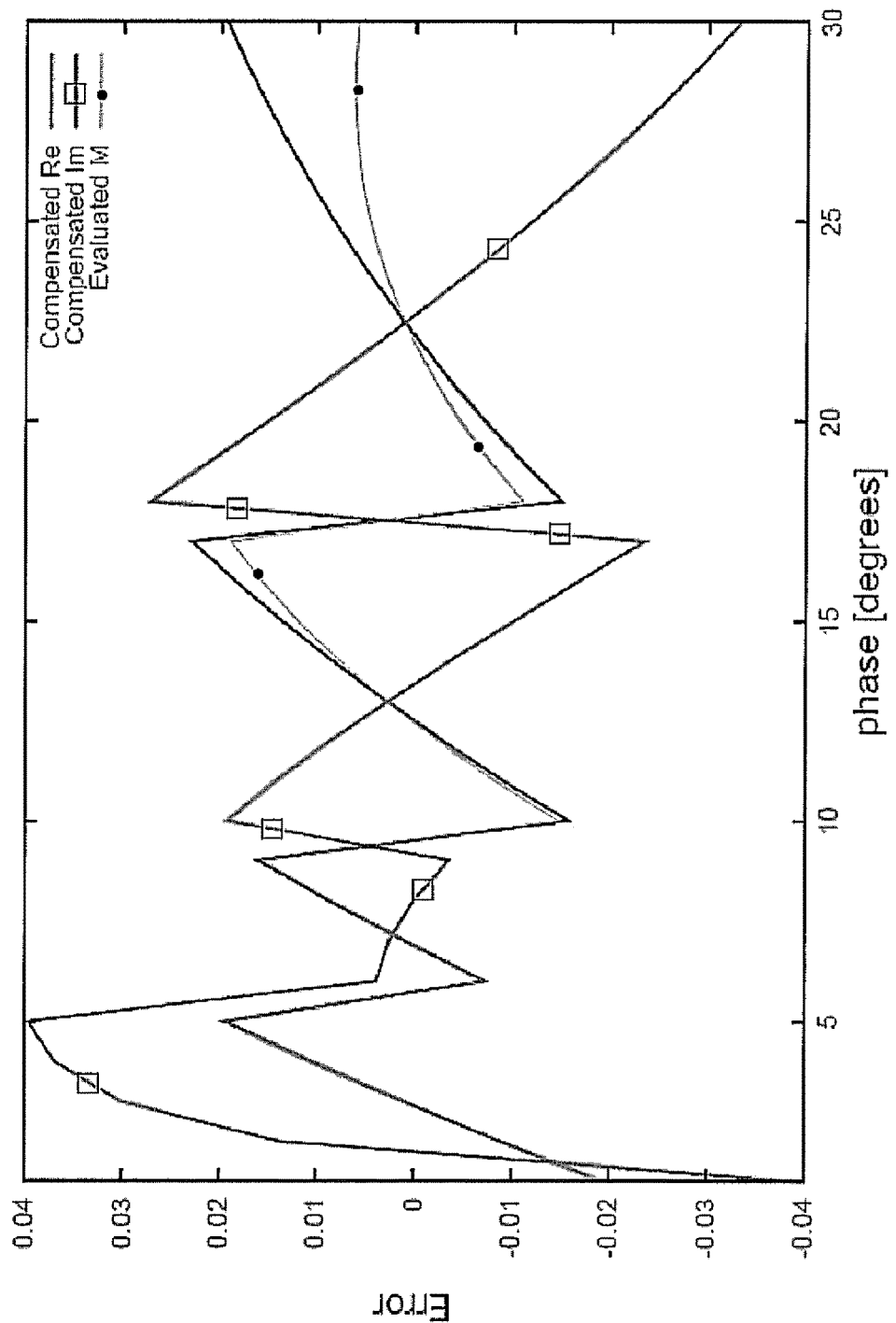
FIG. 14 is a graph of the error on the estimations of the real part and of the imaginary part and of the evaluated modulus of the impedance vs. the phase of the impedance in the complex domain when a compensation technique is implemented.

Substantially, according to this embodiment, the phase of the bioimpedance is used as an indicator that allows adjustment of the values of the parameters $b_R$ and $b_I$. Exemplary percentage error characteristics vs. the phase of the bioimpedance on the estimated real part ReC and imaginary part ImC of the bioimpedance, and the estimated modulus M of the bioimpedance obtained using the above method are compared in the graph of FIG. 14.

The phase of the bioimpedance may not be used as the indicator that allows adjustment of the parameters $b_R$ and $b_I$. Instead, any quantity tied to the phase with a bijective law may be used.

Figure 13A:
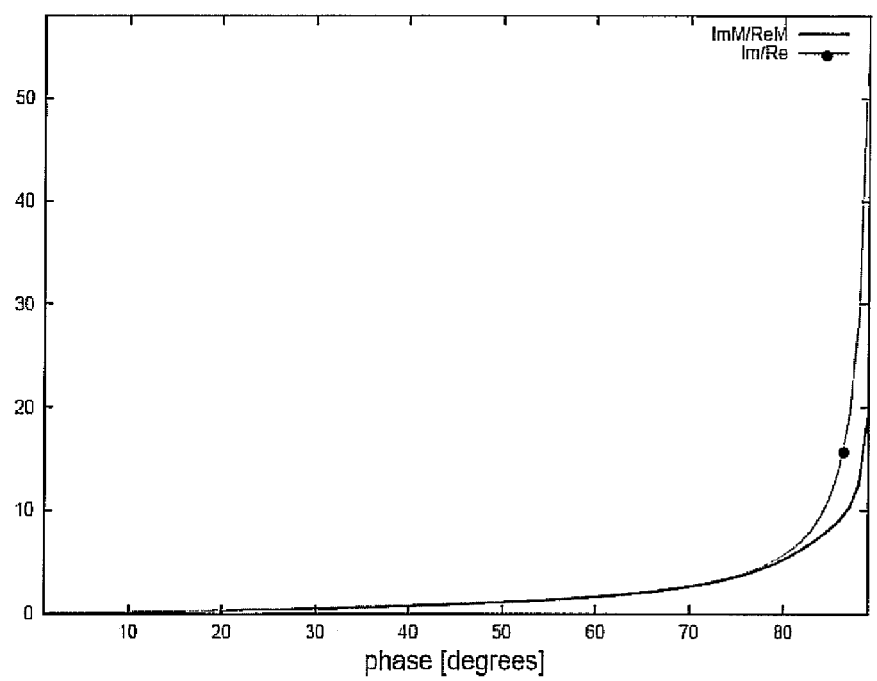
FIG. 13*a* is a graph of the corrected and the uncorrected ratio between the estimations of the real part and of the imaginary part vs. the phase of the impedance in the complex domain.
Figure 13B:
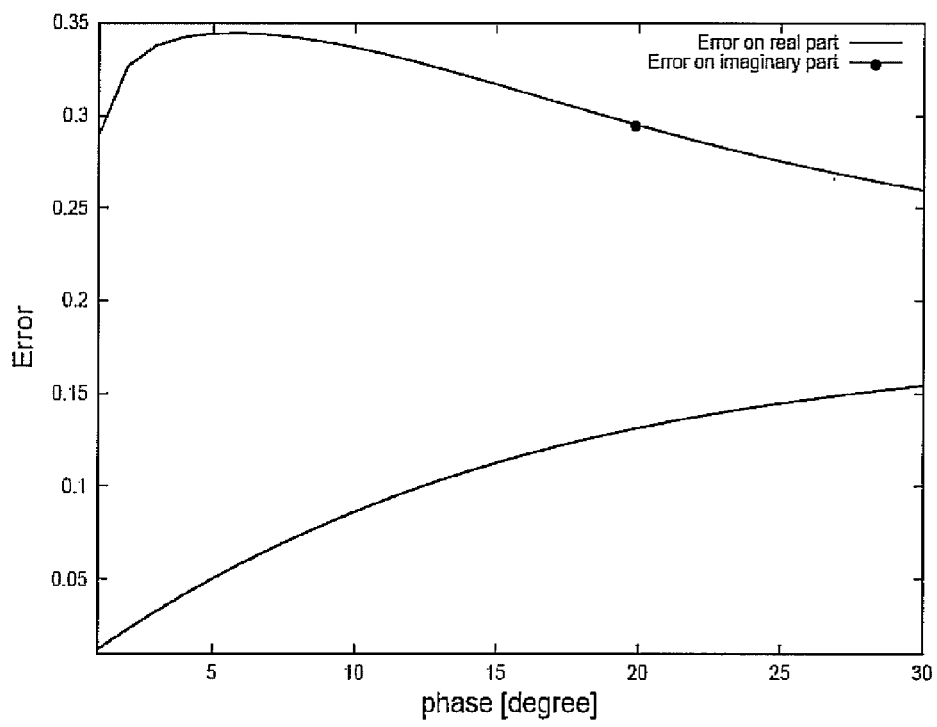
FIG. 13*b* is a graph of the error on the estimations of the real part and of the imaginary part vs. the phase of the impedance in the complex domain.

Referring to the graph in FIG. 13a, it is possible to notice that the ratio $V_{ImM}/V_{ReM}$ is bijectively tied to the phase of the bioimpedance, i.e. by knowing the ratio $V_{ImM}/V_{ReM}$ it is possible to determine the phase of the bioimpedance, and thus to adjust the values of the parameters $b_R$ and $b_I$ to estimate the effective ratio Im/Re between the imaginary part and the real part of the bioimpedance. The percentage error in approximating the effective real part and imaginary part with the values $V_{ImM}$ and $V_{ReM}$ is shown in the graph of FIG. 13b.

Accordingly, the real part and the imaginary part of the bioimpedance are calculated with the following parametric equations:

$$ReC = b_R * V_{ReM} + C_R * V_{ImM}$$

$$ImC = b_I * V_{ImM} + c_I * V_{ImM}^2$$

being $c_R$ and $c_I$ null, wherein the values of the parameters $b_R$ and $b_I$ are adjusted according to the following procedure: preliminarily filling-in a look-up table of heuristically determined values of the parameters $b_R$ and $b_I$ in function of ratios between the demodulated signals first $V_{ReM}$ and second $V_{ImM}$; calculating the ratio between the demodulated signals first $V_{ReM}$ and second $V_{ImM}$; and updating the values of the parameters $b_R$ and $b_I$ with the values stored in the look-up table in correspondence of the calculated ratio.

That which is claimed is:

1. A device for generating an output signal representative of an electrical impedance of biologic tissue comprising:
    a plurality of electrodes configured to contact the biologic tissue and generate a differential voltage thereon;
    a first circuit coupled to said plurality of electrodes and configured to force an oscillating input signal therethrough;
    a differential amplitude modulation (AM) demodulator directly coupled to said plurality of electrodes without intervening amplification circuitry therebetween, and configured to demodulate the differential voltage, and generate a base-band signal representative of the demodulated differential voltage, the differential AM demodulator having a first input terminal coupled to a first one of the plurality of electrodes and a second input terminal coupled to a second one of the plurality of electrodes:
    an amplifier configured to amplify the base-band signal, the amplifier having an inverting terminal coupled to a first output terminal of the differential AM demodulator, and a non-inverting terminal coupled to a second output terminal of the differential AM demodulator: and
    an output circuit downstream from the amplifier and configured to generate the output signal representative of the electrical impedance as a function of an output of the amplifier, wherein the differential AM demodulator comprises a first pair of switches and a second pair of switches controlled in phase opposition to each other.

2. The device of claim 1, wherein said first circuit is configured to generate the oscillating input signal comprising a square wave input signal; and wherein said differential AM demodulator is configured to perform AM demodulation based upon a square-wave demodulation signal.

3. The device of claim 1, wherein the amplifier is configured to generate a first output signal indicative of an alternating current (AC) component of a real part of the electrical impedance and a second output signal indicative of a direct current (DC) component of the real part of the electrical impedance.

4. The device of claim 3, wherein the output circuit comprises a digital circuit configured to process the first output signal and the second output signal, and generate the output signal representative of the electrical impedance.

5. The device of claim 1, wherein the first pair of switches comprises a first switch and a second switch, the first switch of the first pair of switches being coupled between the first input terminal of the differential AM demodulator and the first output terminal of the differential AM demodulator, the second switch of the first pair of switches being coupled between the second input terminal of the differential AM demodulator and the second output terminal of the differential AM demodulator.

6. The device of claim 1, wherein the second pair of switches comprises a first switch and a second switch, the first switch of the second pair of switches being coupled between the second input terminal of the differential AM demodulator and the first output terminal of the differential AM demodulator, the second switch of the second pair of switches being coupled between the first input terminal of the differential AM demodulator and the second output terminal of the differential AM demodulator.

7. A device for generating an output signal representative of an electrical impedance of a biological tissue, the device comprising:
a plurality of electrodes configured to contact the biological tissue;
a current generator coupled to a first one and a second one of the plurality of electrodes, the current generator being configured to force an oscillating current through the first one and the second one of the plurality of electrodes;
a differential amplitude modulation (AM) demodulator having a first input terminal and a second input terminal coupled to a third one and a fourth one of the plurality of electrodes, respectively, the differential AM demodulator being configured to demodulate a differential voltage between the third one and the fourth one of the plurality of electrodes, the differential AM demodulator being further configured to generate a base-band signal representative of the demodulated differential voltage;
an amplifier having a first input terminal coupled to a first output terminal of the differential AM demodulator, and a second input terminal coupled to a second output terminal of the differential AM demodulator, the amplifier being configured to amplify the base-band signal; and
a processing circuit configured to generate the output signal representative of the electrical impedance of the biological tissue based on an output of the amplifier, wherein the differential AM demodulator comprises a first pair of switches and a second pair of switches controlled in phase opposition to each other.

8. The device of claim 7, wherein the current generator comprises a first current source coupled between a first reference voltage and the first one of the plurality of electrodes, the current generator further comprising a second current source coupled between the second one of the plurality of electrodes and a second reference voltage.

9. The device of claim 8, wherein the second reference voltage comprises a ground potential.

10. The device of claim 7, wherein the differential AM demodulator is coupled to the third one and the fourth one of the plurality of electrodes without intervening amplification circuitry therebetween.

11. The device of claim 7, wherein the first input terminal and the second input terminal of the amplifier comprise a non-inverting terminal and an inverting terminal of the amplifier, respectively.

12. The device of claim 7, wherein the output of the amplifier comprises a first output signal indicative of an alternating current (AC) component of a real part of the electrical impedance and a second output signal indicative of a direct current (DC) component of the real part of the electrical impedance.

13. The device of claim 7, wherein the first pair of switches comprises a first switch and a second switch, the first switch of the first pair of switches being coupled between the first input terminal of the differential AM demodulator and the first output terminal of the differential AM demodulator, the second switch of the first pair of switches being coupled between the second input terminal of the differential AM demodulator and the second output terminal of the differential AM demodulator.

14. The device of claim 7, wherein the second pair of switches comprises a first switch and a second switch, the first switch of the second pair of switches being coupled between the second input terminal of the differential AM demodulator and the first output terminal of the differential AM demodulator, the second switch of the second pair of switches being coupled between the first input terminal of the differential AM demodulator and the second output terminal of the differential AM demodulator.

15. A device for generating an output signal representative of an electrical impedance of a biological tissue, the device comprising:
a plurality of electrodes configured to contact the biological tissue;
a first circuit coupled to the plurality of electrodes and configured to force a square-wave input signal through the plurality of electrodes;
a differential amplitude modulation (AM) demodulator having a first input terminal and a second input terminal respectively coupled to a first one and a second one of the plurality of electrodes, the differential AM demodulator being configured to demodulate a differential voltage between the first one and the second one of the plurality of electrodes, the differential AM demodulator being further configured to generate a base-band signal representative of the demodulated differential voltage;
an differential amplifier configured to amplify the base-band signal, the differential amplifier having an inverting terminal coupled to a first output terminal of the differential AM demodulator, and a non-inverting terminal coupled to a second output terminal of the differential AM demodulator; and
a digital circuit configured to process an output of the differential amplifier and generate the output signal representative of the electrical impedance of the biological tissue, wherein the differential AM demodulator comprises a first pair of switches and a second pair of switches controlled in phase opposition to each other.

16. The device of claim 15, wherein the differential AM demodulator is coupled to the first one and the second one of the plurality of electrodes without intervening amplification circuitry therebetween.

17. The device of claim 15, wherein the output of the differential amplifier comprises a first output signal indicative of an alternating current (AC) component of a real part of the electrical impedance and a second output signal indicative of a direct current (DC) component of the real part of the electrical impedance.

* * * * *